United States Patent [19]
Vesely et al.

[11] Patent Number: 5,795,298
[45] Date of Patent: Aug. 18, 1998

[54] SYSTEM FOR SHARING ELECTROCARDIOGRAM ELECTRODES AND TRANSDUCERS

[75] Inventors: Ivan Vesely, Cleveland Heights, Ohio; Marshall Edge, London, Canada

[73] Assignee: Sonometrics Corporation, London, Canada

[21] Appl. No.: 813,924

[22] Filed: Mar. 7, 1997

Related U.S. Application Data

[63] Continuation-in-part of PCT/CA96/00194, Mar. 28, 1996 published as WO96/31753, Oct. 10, 1996, which is as continuation-in-part of Ser. No. 411,959, Mar. 28, 1995, Pat. No. 5,515,853.

[51] Int. Cl.$^6$ .................................................. A61B 8/00
[52] U.S. Cl. ................................... 600/450; 600/374
[58] Field of Search .................... 600/439, 446, 600/447, 450, 462, 466, 467, 471, 509, 510, 372, 373, 374, 381; 607/122

[56] References Cited

U.S. PATENT DOCUMENTS

| | | |
|---|---|---|
| 4,173,228 | 11/1979 | VanSteenwyk et al. |
| 4,304,239 | 12/1981 | Perlin |
| 4,431,005 | 2/1984 | McCormick |
| 4,444,195 | 4/1984 | Gold |
| 4,499,493 | 2/1985 | Nishimura |
| 4,522,212 | 6/1985 | Gelinas et al. |
| 4,573,473 | 3/1986 | Hess |
| 4,613,866 | 9/1986 | Blood |
| 4,628,937 | 12/1986 | Hess et al. |
| 4,649,924 | 3/1987 | Taccardi |
| 4,697,595 | 10/1987 | Breyer et al. |
| 4,699,147 | 10/1987 | Chilson et al. |
| 4,777,955 | 10/1988 | Brayton et al. |
| 4,812,976 | 3/1989 | Lundy |
| 4,821,731 | 4/1989 | Martinelli et al. |
| 4,899,750 | 2/1990 | Ekwall |
| 4,922,912 | 5/1990 | Watanabe |

(List continued on next page.)

FOREIGN PATENT DOCUMENTS

| | | |
|---|---|---|
| 0 152 905 | 8/1985 | European Pat. Off. |
| 92301264.5 | 2/1992 | European Pat. Off. |
| 0 591 899 | 10/1993 | European Pat. Off. |
| 3904914 | 8/1990 | Germany |
| 41 19 150 | 12/1992 | Germany |
| US94/08352 | 7/1994 | WIPO |
| US94/11298 | 10/1994 | WIPO |
| US95/01103 | 1/1995 | WIPO |
| PCT/CA96/00194 | 3/1996 | WIPO |

OTHER PUBLICATIONS

Davis J.W., Improved Arrival Time Detection for Cardiac Pulse Transit Sonomicrometry, *Computers in Cardiology 1996*, pp. 145–459, 1996.

Morse, Wayne, Medical Electronics, *IEEE Spectrum*, pp. 99–102, Jan. 1997.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Tachycardia during Endocardial Pacing. II. Role of Pace–Mapping to Localize Origin of Ventricular Tachycardia, *The American Journal of Cardiology*, vol. 50, pp. 11–22, Jul. 1982.

(List continued on next page.)

*Primary Examiner*—George Manuel
*Attorney, Agent, or Firm*—Benesch, Friedlander Coplan & Aronoff LLP

[57] ABSTRACT

A device having a combined electrode (20) and position tracking transducer (30) mounted to a surgical instrument, such as a catheter (10). In a preferred embodiment of the invention, the electrode (20) serves dual functions, namely as a standard ECG electrode for communicating an ECG voltage, and as an electrode transducer, such as a conductor for a transducer. The combined ECG electrode and position tracking transducer minimizes the amount of space needed on the surgical instrument and the number of required components.

18 Claims, 2 Drawing Sheets

U.S. PATENT DOCUMENTS

| | | | |
|---|---|---|---|
| 4,932,414 | 6/1990 | Coleman et al. | 128/600.09 |
| 4,940,064 | 7/1990 | Desai . | |
| 4,945,305 | 7/1990 | Blood . | |
| 5,000,190 | 3/1991 | Petre . | |
| 5,012,814 | 5/1991 | Mills et al. . | |
| 5,016,173 | 5/1991 | Kenet et al. | 382/128 |
| 5,025,786 | 6/1991 | Siegel . | |
| 5,041,973 | 8/1991 | Lebron et al. . | |
| 5,042,486 | 8/1991 | Pfeiler et al. | 128/653 |
| 5,054,492 | 10/1991 | Scribner et al. . | |
| 5,054,496 | 10/1991 | Wen et al. . | |
| 5,056,517 | 10/1991 | Fenici . | |
| 5,081,993 | 1/1992 | Kitney et al. . | |
| 5,104,393 | 4/1992 | Isner et al. . | |
| 5,154,501 | 10/1992 | Svenson et al. . | |
| 5,156,151 | 10/1992 | Imran . | |
| 5,158,092 | 10/1992 | Glace . | |
| 5,161,536 | 11/1992 | Vilkomerson et al. . | |
| 5,172,699 | 12/1992 | Svenson et al. . | |
| 5,220,924 | 6/1993 | Frazin . | |
| 5,222,501 | 6/1993 | Ideker et al. . | |
| 5,246,016 | 9/1993 | Lieber et al. . | |
| 5,295,484 | 3/1994 | Marcus et al. . | |
| 5,297,549 | 3/1994 | Beatty et al. . | |
| 5,323,781 | 6/1994 | Ideker et al. | 607/122 |
| 5,341,807 | 8/1994 | Nardella . | |
| 5,357,956 | 10/1994 | Nardella . | |
| 5,391,199 | 2/1995 | Ben-Haim . | |
| 5,443,489 | 8/1995 | Ben-Haim . | |
| 5,480,422 | 1/1996 | Ben-Haim . | |
| 5,515,853 | 5/1996 | Smith et al. . | |
| 5,517,990 | 5/1996 | Kalfas et al. . | |
| 5,546,951 | 8/1996 | Ben-Haim . | |

OTHER PUBLICATIONS

Witkowski et al., An Automated Simultaneous Transmural Cardiac Mapping System. *American Journal of Physiology*, vol. 247, pp. H661–H668, 1984.

Fann et al., Endocardial Activation Mapping and Endocardial Pace–Mapping Using a Balloon Apparatus. *American Journal of Cardiology*, vol. 55, pp. 1076–1083, Apr. 1, 1985.

Tweddell et al., Potential Mapping in Septal Tachycardia: Evaluation of a New Intraoperative Mapping Technique; *Circulation*, vol. 80 (Supplement I), No. 3, pp. I–97 –I–108, Sep. 1989.

Hauer et al., Endocardial Catheter Mapping: Wire Skeleton Techniques for Representation of Computed Arrhythmogenic Sites Compared with Intraoperative Mapping, *Circulation*, vol. 74, No. 6, pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations. *Pace*, vol. II, pp. 449–459, Apr. 1988.

Jackman et al., New Catheter Techniques for Recording Left Free–Wall Accessory Atrioventricular Pathway Activation, *Circulation*, vol. 78, No. 3, pp. 598–611, Sep. 1988.

Shenasa et al., Cardia Mapping, Part I: Wolff–Parkinson––White Syndrome. *Pace*, vol. 13, pp. 223–230, Feb. 1990.

Scheinman et al., Current Role of Catheter Ablative Procedures in Patients with Cardiac Arrhythmias. *Circulation*, vol. 83, No. 6, pp. 2146–2153, Jun. 1991.

Buckles et al., Computer–Enhanced Mapping of Activation Sequences in the Surgical Treatment of Supraventricular Arrhythmias. *Pace*, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome. *Journal of American College of Cardiologists*, vol. 17, No. 2, pp. 403–408, Feb. 1991.

Kaltenbrunner et al., Epicardial and Endocardial Mapping of Ventricular Tachycardia in Patients with Myocardial Infarction. *Circulation*, vol. 83, No. 3, pp. 1058–1071, Sep. 1991.

Masse et al., A Three–Dimensional Display for Cardiac Activation Mapping. *Pace*, vol. 14, Pt. 1, pp. 538–545, Apr. 1991.

Desai et al., Orthogonal Electrode Catheter Array for Mapping of Endocardial Focal Site of Ventricular Activation. *Pace*, vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System. *Pace*, vol. 15, pp. 854–858, Jun. 1992.

Chen et al., Reappraisal of Electrical Cure of Atrioventricular Nodal Reentrant Tachycardia –Lesions from a Modified Catheter Albation Technique. *International Journal of Cardiology*, vol. 37, pp. 51–60, 1992.

Chen et al., Radiofrequency Catheter Albaltion For Treatment of Wolff–Parkinson–White Syndrome–Short–and Long–Term Follow–up. *International Journal of Cardiology*, vol. 37, pp. 199–207, 1992.

Scheinman, North American Society of Pacing and Electrophysiology (NASPE) Survey on Radiofrequency Catheter Ablation: Implications for Clinicians, Third Party Insurers, and Government Regulatory Agencies. *Pace*, vol. 15, pp. 2228–2231, Dec. 1992.

Silka et al., Phase Image Analysis of Anomalour Ventricular Activation in Petiatric Patients with Pre–excitation Syndromes or Ventricular Tachycardia. *American Heart Journal*, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, *Lea & Febiger*, Malvern, Pa., 1993.

Holt et al., Ventricular Arrhythmias –A Guide to Their Localization. *British Heart Journal*, vol. 53, pp. 417–430, 1985.

Joseph et al., Role of Catheter Mapping in the Preoperative Evaluation of Ventricular Tachycardia. *American Journal of Cardiology*, vol. 40, pp. 207–220, Jan. 1982.

Kucher et al., Electrocardiographic Localization of the Site of Ventricular Tachycardia in Patients with Prior Myocardial Infarction. *JACC*, vol. 13, No. 4 pp. 893–900.

Page, Surgical Treatment of Ventricular Tachycardia: Regional Cryoablation Guided by Computerized Epicardial and Endocardial Mapping. *Circulation*, vol. 80, (Supplement I), No. 3, pp. 1124 –I–134, Sep. 1989.

Meyer et al., Application of Sonomicrometry and Multidimensional Scaling to Cardiac Catheter Tracking. *Transactions on BioMedical Engineering*, vol. 44 No. 11, pp. 1061–1067, Nov. 1997.

SYSTEM FOR SHARING ELECTROCARDIOGRAM ELECTRODES AND TRANSDUCERS

RELATED APPLICATIONS

This is a continuation-in-part of International Application Ser. No. PCT/CA96/00194, filed on Mar. 28, 1996 and now PCT/WO96/31753, which is a continuation in part of Ser. No. 08/411,959 filed Mar. 28, 1995, now U.S. Pat. No. 5,515,853.

FIELD OF THE INVENTION

The present invention relates generally to a surgical instrument having both electrodes and transducers mounted thereupon, and more particularly to a catheter having both ECG electrodes and ultrasonic transducers mounted thereupon and sharing the same physical entity.

BACKGROUND OF THE INVENTION

In electrophysiology applications, mapping and ablating catheters are inserted into a patient's body and passed along blood vessels until they enter the heart chambers. At that point, the electrocardiogram is mapped by placing the catheter against the internal wall of the heart chambers, the ventricles or the atria. According to the prior art, the mapping process involves visualizing the mapping catheter inside the heart using continuous fluoroscopy, which creates a shadow of the catheter that moves with the heart as the physician manipulates the catheter.

Since the manipulation of these types of catheters is difficult and time consuming, and fluoroscopy subjects patients and doctors to considerable doses if x-ray, an ultrasound based catheter guidance system, such as described in U.S. Pat. No. 5,515,853 and incorporated herein by reference, is used to display the position and motion of the catheter as a 3-D graphic. The catheter guidance system makes use of transit time ultrasound to measure the distance between an array of ultrasonic transducers. Some of the transducers (i.e. "mobile transducers") are mounted to catheters inserted into the patient's body, and other transducers are affixed to the patient at fixed locations (i.e. "reference transducers") to provide internal and/or external reference frames. A large matrix of distances between many combinations of transducers is obtained many times per second, and then converted into 3-dimensional x,y,z coordinates for each transducer. The motion of the catheter affixed with such ultrasonic transducers can then be tracked in 3-D space, relative to the position of the reference transducers.

Using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal), that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received.

A typical electrophysiology catheter takes the form of a polymeric tube with metallic electrodes arranged as rings near its distal end. For each electrode, there is an electrical conductor that runs the length of the catheter shaft and exits at a connector at the proximal end of the catheter to transmit signals to and from the electrode. In order to track the position of the catheter using an ultrasonic catheter guidance system, the catheter must be fitted with appropriate ultrasonic transducers (i.e. "mobile transducers"). These transducers take up space near the mapping portion of the catheter where the electrodes are located, and must also have electrical conductors within the catheter to transmit signals to and from the transducers. In most cases, each ultrasonic transducer requires two additional conductors within the catheter.

The additional space occupied by -the ultrasonic transducers, as well as the many additional conductors needed to be passed through the catheter are undesirable. In this respect, the distal end of the catheter is often intended to deflect, and through the addition of rigid members (i.e., transducers) to the catheter, the ability of the catheter to easily bend is reduced. Moreover, it is important to note that there is finite space inside a catheter for electrodes. Therefore, there is a need to minimize the space taken by the ultrasonic transducers on the catheter, as well as a need to reduce the number of extra conductors within the catheter shaft.

The present invention overcomes these and other drawbacks of prior devices and provides a method and apparatus which minimizes the amount of space needed on a catheter to include ultrasonic transducers, and minimizes the number of electrical conductors arranged within the catheter shaft.

SUMMARY OF THE INVENTION

According to the present invention there is provided an instrument having a combined electrode and transducer sharing the same physical entity.

It is an object of the present invention to provide a merged electrode and transducer mountable to an instrument, wherein the electrode is adapted for mapping or ablation and the transducer is suitable for tracking the position of the instrument.

It is another object of the present invention to provide an instrument having an electrode and a transducer arranged in the same physical entity.

It is another object of the present invention to provide a catheter having a mapping or ablation electrode and an ultrasonic transducer, wherein the space taken up by the ultrasonic transducer on the catheter is minimized.

It is still another object of the present invention to provide a catheter having a combined mapping or ablation electrode and ultrasonic transducer, wherein the number of conductors located within the catheter shaft are minimized.

It is yet another object of the present invention to provide a catheter having a combined mapping or ablation electrode and ultrasonic transducer, wherein conductors between the mapping electrodes and ultrasonic transducers are shared.

These and other objects will become apparent from the following description of a preferred embodiment of the present invention taken together with the accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
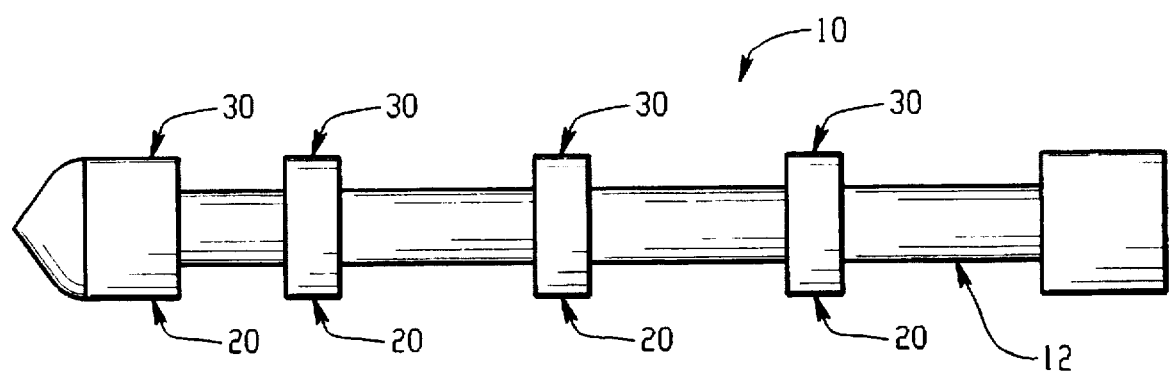
FIG. 1 is a side perspective view of a catheter illustrating a preferred embodiment of the present invention.
Figure 2:
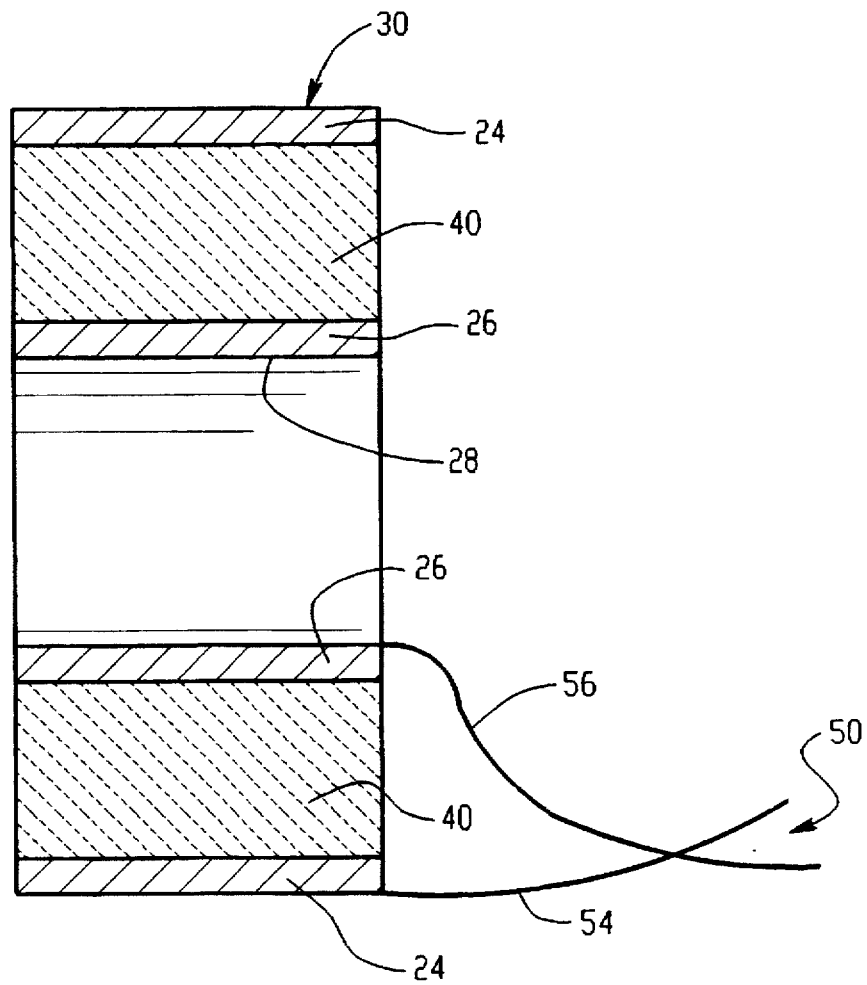
FIG. 2 is a sectional side view of the catheter shown in FIG. 1.

Referring now to the drawings wherein the showings are for the purposes of illustrating a preferred embodiment of the invention only and not for purposes of limiting same. FIG. 1 shows a catheter 10 having ultrasonic transducers 30 and electrodes 20 mounted to the distal end of a catheter shaft 12. Transducers 30 are comprised of an annular outer conductor 24, an annular inner conductor 26 and a ring of piezoelectric material 40, which is arranged therebetween, as shown in FIG. 2. Outer conductor 24 also serves as electrode 20. Piezoelectric material preferably takes the form of a piezoelectric crystal. By using outer conductor's surfaces 24 as mapping electrodes 20, no additional space is required on the catheters for the transducers 30. It should be appreciated that outer conductor 24 and inner conductor 26 may take the form of a metallic plating or film.

While a preferred embodiment of the present invention will be described with reference to "mapping" electrodes, electrodes 20 may take the form of other types of electrodes including ablation electrodes, mapping baskets, plates, and strips. Moreover, other types of instruments can be substituted for catheter 10, including probes, sensors, needles and the like.

Shaft 12 of catheter 10 is arranged through opening 28 formed by annular inner conductor 26. A pair of electrode/transducer conductor leads 50 extend respectively from outer conductor 24 and inner conductor 26. Conductor leads 50 extend through ducts formed in catheter 10. The first lead is a ground conductor lead 54 and the second lead is a power conductor lead 56.

Figure 3:
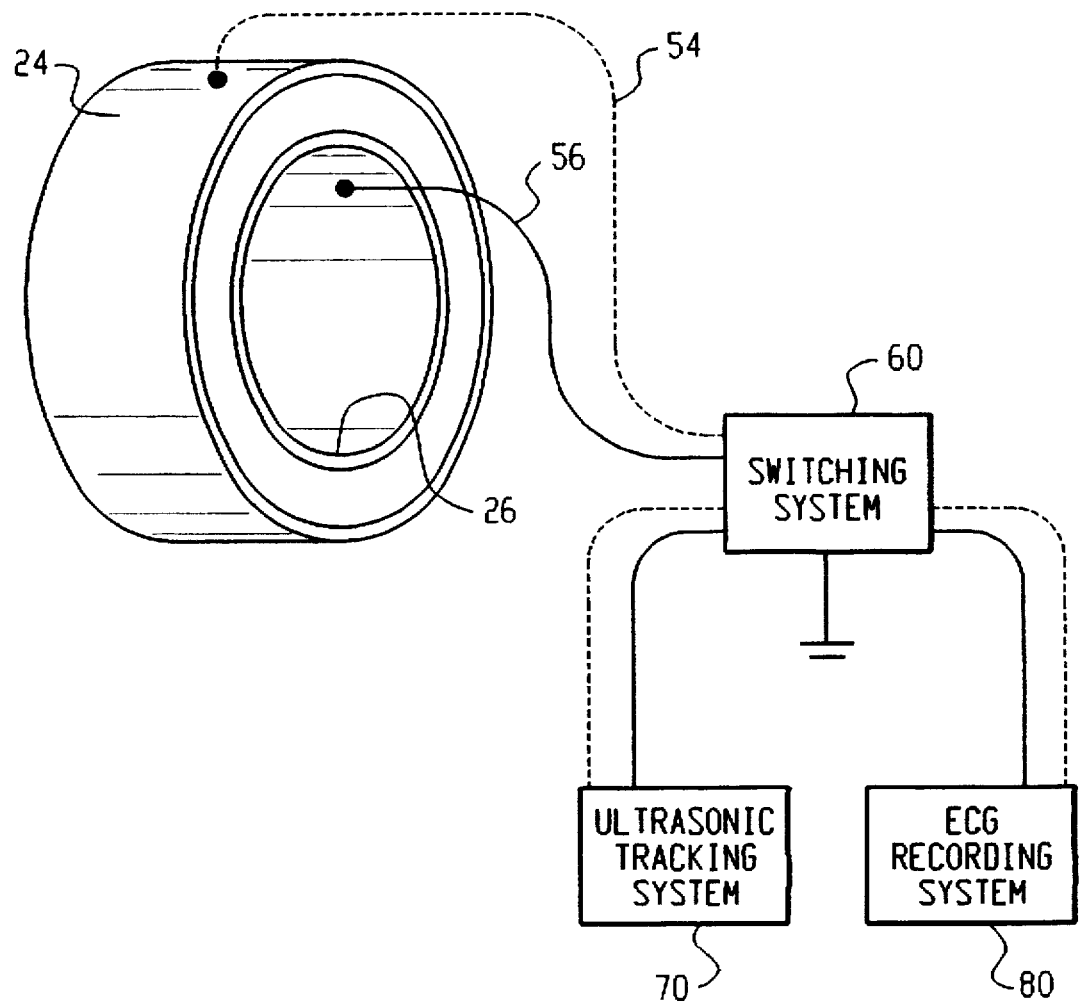
FIG. 3 is a block diagram showing the circuitry of the present invention.

Outer conductor 24 serves as mapping electrode 20 and as one of two conductors for transducer 30. Accordingly, outer conductor 24 has a dual role of serving both the mapping and tracking functions of catheter 10. During an ECG recording mode of operation, outer conductor 24 will sense the voltage produced by the heart and deliver it through the catheter to external amplifiers. In an ultrasonic tracking mode of operation, outer conductor 24 carries electrical signals to and from transducers 30. In this respect, outer conductor 24 communicates electrical signals from tracking system 70 (e.g., a sonomicrometer) to "fire" transmitter transducers, and communicates electrical signals from receiver transducers, indicating the receipt of a transmitted sound wave. Since these two modes of operation cannot take place simultaneously, a switching system 60 is provided to electrically isolate one mode from the other, as will be described with reference to FIG. 3. Therefore, during an ECG recording mode, tracking system 70 is inhibited from "firing" transducers 30, and the conductor path is switched to the voltage amplifiers that detect the ECG. It should be noted that the term "firing" refers to the action of energizing a transducer to oscillate (thus producing an ultrasonic sound wave) by sending a voltage spike or the impulse function to the transducer.

During an ultrasonic tracking mode, the ECG recording amplifiers are switched out and ultrasonic tracking system 70 is activated. It should be appreciated that during the ultrasonic tracking mode, the voltage that is applied to transducers 30 can be as high as a 160 volts. Therefore, it is imperative that this voltage does not appear at outer conductor 24 which is in contact with the patient's heart. To ensure this, the potential of the patient and the potential of the outer conductor 24 are made equal. In this respect, outer ground lead 54 is provided to electrically ground the outer conductor 24, as well as the patient, during a "firing" cycle. Accordingly, the voltage at inner conductor 26 can be as high as 160 volts, while voltage at outer conductor 24, relative to the patient, is zero.

It should be appreciated that the foregoing arrangement of potential switching can be enabled through the appropriate solid state devices, or through micro reed switches that are configured so that the default condition grounds outer ring conductor 24, for the sake of patient safety. The system also has the provision for testing the condition of switching system 60, so that an automatic power down of ultrasonic tracking system 70 is initiated that the patient and outer conductor 24 are not at the same potential (i.e., ground).

The foregoing is a description of the specific embodiment of the present invention. It should be appreciated that this embodiment is described for the purpose of illustration only and that numerous alterations and modifications may be practiced by those skilled in the art without departing from the spirit and scope of the present invention. For instance, the transducers may take the form of electromagnetic transducers and the ultrasonic tracking system may take the form of an electromagnetic tracking system. Moreover, the mapping catheters may be other types of catheters (e.g., ablation catheters) or other surgical instruments (e.g., probes, sensors, etc.). It is intended that all such modifications and alterations be included insofar as they come within the scope of the invention as claimed or the equivalents thereof

Having thus described the invention, it is now claimed:

1. A catheter arrangement capable of providing data signals for ECG recording and ultrasonic tracking, comprising:

a catheter having a catheter shaft;
a plurality of detection means arranged along the catheter shaft comprising:
  inner conductor means formed on the catheter shaft;
  outer conductor means surrounding the inner conductor means;
  a piezoelectric material arranged between the inner conductor means and the outer conductor means;

ground conductor means extending from one of the inner conductor means and the outer conductor means; and power conductor means extending from one of the inner conductor means and the outer conductor means, wherein the inner and outer conductor means and piezoelectric material serve as transducer means and the outer conductor means serves as an electrode.

2. A catheter arrangement according to claim 1, wherein the arrangement further comprises switching means for switching between an ECG recording mode and an ultrasonic tracking mode, wherein during the ECG recording mode the power conductor means is operatively connected to a voltage amplifier means for communicating a voltage from a heart, and in the ultrasonic tracking mode the ground conductor means is grounded and a voltage is applied to the power conductor means for firing the piezoelectric material.

3. A catheter arrangement as defined in claim 1, wherein the system further comprises ultrasonic tracking means having a sonomicrometer, and ECG recording means.

4. A catheter arrangement as defined in claim 3, wherein said switching means alternates between firing the transducer means and recording the voltage applied to said outer conductor means.

5. A catheter arrangement as defined in claim 4, wherein said switching means includes testing means for determining whether the potential applied to said outer conductor means is generally equal to the potential of a patient in which the catheter is located, and means for preventing the firing of the transducer means if the potentials are not equal.

6. A catheter arrangement as defined in claim 5, wherein said means for preventing the firing is a reed switch.

7. A catheter arrangement as defined in claim 4, wherein said switching means includes testing means for determining a first potential applied to the outer conductor means and a second potential of a patient in which the catheter is located, and means for preventing the firing of the transducer means if the first and second potentials are not approximately zero.

8. A catheter for use with an ECG recording and ultrasonic tracking device, the catheter comprising:

an elongated catheter shaft means;

a plurality of detection means arranged along the shaft means, each of the detection means comprising:
inner conductor means arranged on the shaft means,
outer conductor means surrounding the inner conductor means,
piezoelectric material arranged between the inner conductor means and the outer conductor means,
first conductor lead means extending from the outer conductor means, and
second conductor lead means extending from the inner conductor means;

wherein the inner conductor means, the outer conductor means and the piezoelectric material therebetween provide an ultrasonic transducer means, and the outer conductor means provides a mapping electrode; and switching means for switching between an ECG recording mode and an ultrasonic tracking mode, wherein the outer conductor means is active as the mapping electrode in the ECG recording mode, and the outer conductor means, the inner conductor means, and the piezoelectric material therebetween are active as a transducer means during the ultrasonic tracking mode.

9. A catheter as defined in claim 8, wherein in the ECG recording mode said outer conductor means communicates a voltage from a patient's heart.

10. A catheter as defined in claim 8, wherein during the ultrasonic tracking mode, said inner conductor means is grounded and the outer conductor means receives a voltage to fire the piezoelectric material.

11. A system for ECG recording and position tracking, the system comprising:

instrument means adapted for insertion into an associated body to facilitate conducting a specified surgical procedure, the instrument means including support means;

a plurality of detection means arranged on the support means, each of the detection means comprising:
inner conductor means mounted to the support means,
outer conductor means surrounding the inner conductor means,
piezoelectric material arranged between the inner conductor means and the outer conductor means,
first conductor lead means extending from the inner conductor means, and
second conductor lead means extending from the outer conductor means, wherein the inner conductor means, the outer conductor means and the piezoelectric material therebetween provide an ultrasonic transducer means, and the outer conductor means provides a mapping electrode; and switching means for switching between an ECG recording mode and an ultrasonic tracking mode, wherein the outer conductor means is active as the mapping electrode in the ECG recording mode, and in the ultrasonic tracking mode, the outer conductor means, the inner conductor means, and the piezoelectric material therebetween are active as a transducer means.

12. A system as defined in claim 11, wherein in the ECG recording mode said outer conductor means is adapted to communicate a voltage from an associated patient's heart disposed in the associated body.

13. A system as defined in claim 11, wherein during the ultrasonic tracking mode, said inner conductor means is grounded and the outer conductor means receives a voltage to fire said the piezoelectric material.

14. A system as defined in claim 11, wherein the instrument means is one of the following: mapping catheter, mapping basket, mapping plates, and mapping strips.

15. A system as defined in claim 11, wherein said transducer means is an ultrasonic transducer.

16. A recording and tracking system having a merged electrode and transducer comprising:

an instrument adapted for insertion into an associated body to conduct a surgical procedure, the instrument including support means;

inner conductor means mounted to the support means;

outer conductor means surrounding the inner conductor means;

piezoelectric material arranged between the inner conductor means and the outer conductor means;

first conductor lead means extending from the inner conductor means;

second conductor lead means extending from the outer conductor means;

wherein the inner conductor means, the outer conductor means and the piezoelectric material therebetween form a transducer means, and the outer conductor means forms an electrode; and switching means for switching between the activation of the transducer means and the activation of the electrode, wherein tracking occurs when the transducer means is active and recording occurs when the electrode is active.

17. A system as described in claim 16, wherein said transducer means is an ultrasonic transducer and said electrode is a mapping electrode.

18. A system as described in claim 16, wherein said transducer means is an ultrasonic transducer and said electrode is an ablation electrode.

* * * * *